United States Patent
Ström et al.

[11] Patent Number: 5,450,749
[45] Date of Patent: Sep. 19, 1995

[54] GAS SAMPLING METHOD AND DILUTION TUNNEL THEREFOR

[75] Inventors: Hans Ström, Kode; Roy Ekdahl, Floda, both of Sweden; Edwin S. Harbuck, Shreveport, La.

[73] Assignee: WCI Outdoor Products, Inc., Shreveport, La.

[21] Appl. No.: 219,672

[22] Filed: Mar. 28, 1994

Related U.S. Application Data

[63] Continuation-in-part of Ser. No. 111,843, Aug. 25, 1993.

[51] Int. Cl.⁶ .......................................... G01M 15/00
[52] U.S. Cl. .................................. 73/117.3; 73/23.32
[58] Field of Search ........................... 73/117.3, 23.32

[56] References Cited

U.S. PATENT DOCUMENTS

| | | | |
|---|---|---|---|
| 4,372,155 | 2/1983 | Butler et al. | 73/23.32 |
| 4,534,213 | 8/1985 | Mirikidani | 73/23.32 |
| 4,534,330 | 8/1985 | Osuga et al. | 73/23.32 |
| 4,570,479 | 2/1986 | Sakurai et al. | 73/23.32 |
| 4,574,627 | 3/1986 | Sakurai et al. | 73/23.32 |
| 4,638,658 | 1/1987 | Otobe | 73/117.3 |
| 4,686,846 | 8/1987 | Aramaki | 73/23.32 |
| 4,796,587 | 1/1989 | Nakajima et al. | 73/23.32 |
| 5,231,864 | 8/1993 | Ishida et al. | 73/23.32 |
| 5,255,554 | 10/1993 | Mallebrein et al. | 73/23.32 |

Primary Examiner—Richard E. Chilcot, Jr.
Assistant Examiner—Eric S. McCall
Attorney, Agent, or Firm—Pearne, Gordon, McCoy & Granger

[57] ABSTRACT

Emission gasses from an engine exhaust pipe are collected through an inlet of a dilution tunnel which is an elongated, hollow tube. The inlet is spaced from the exhaust pipe to also admit surrounding air. Ambient air and emissions are mixed in the tunnel by a screen in the tunnel. A probe in the tunnel diverts a portion of the mixture to gas analyzers. Prior to analysis the mixture may be condensed, filtered or otherwise processed. The analysis determines a CO/CO₂ ratio which is used to determine the air/fuel ratio in the engine based on characteristics of the fuel. The air/fuel mixture of the engine is then adjusted to achieve desired performance.

18 Claims, 4 Drawing Sheets

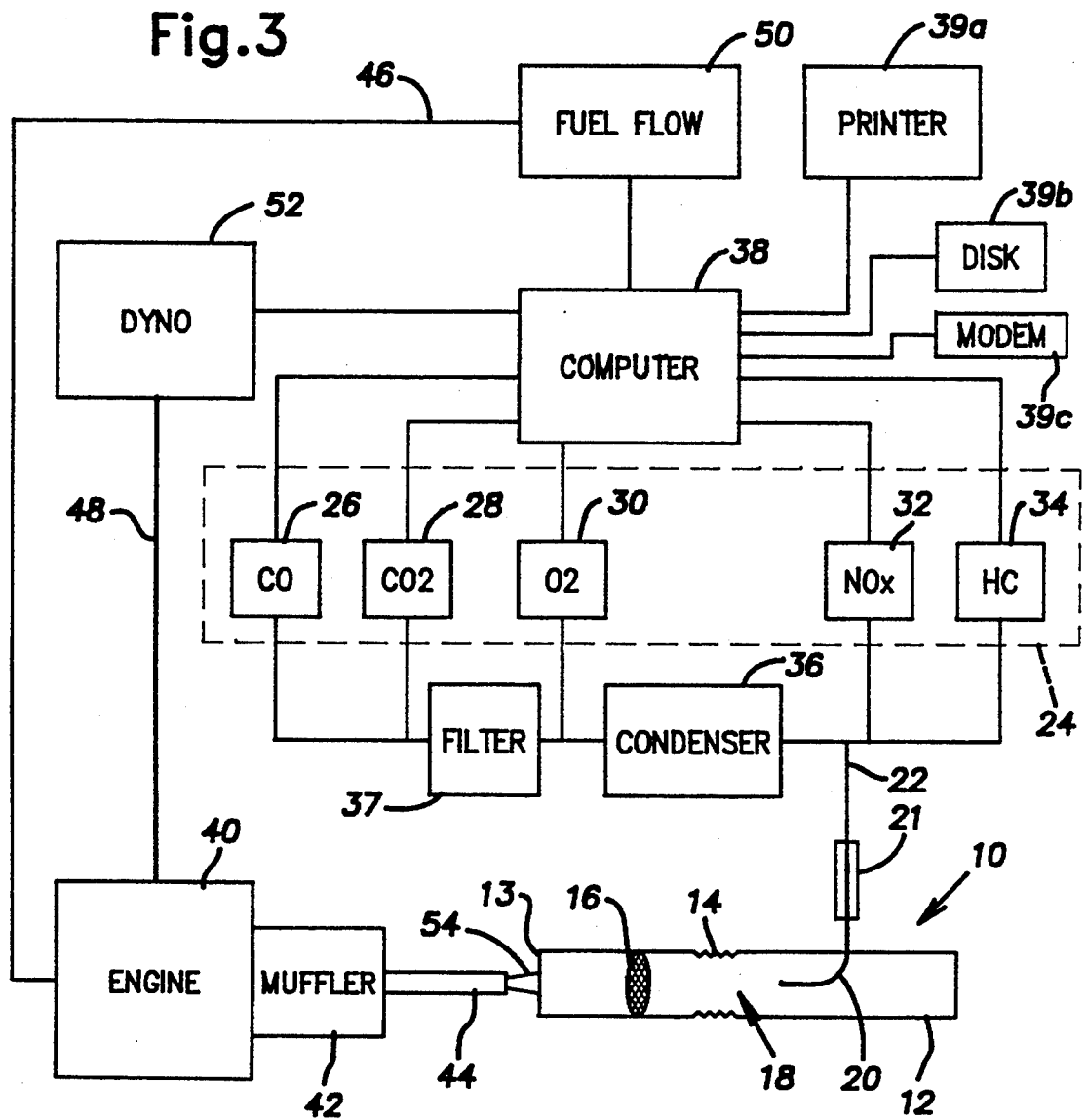
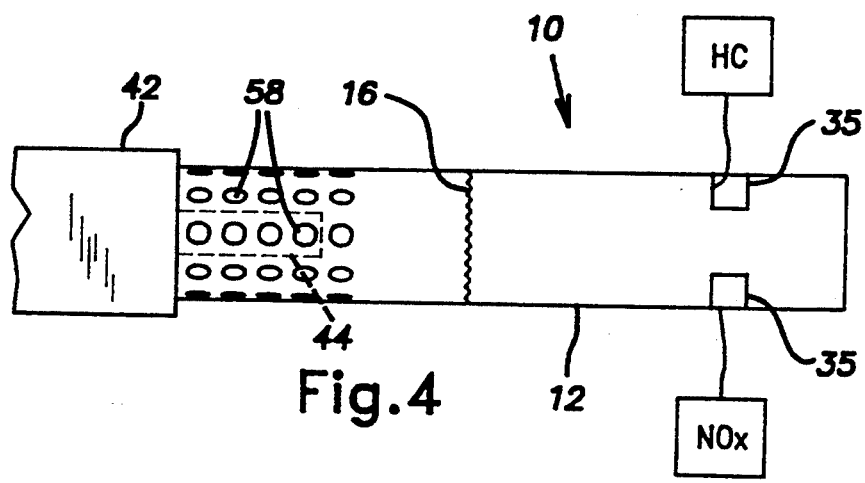

GAS SAMPLING METHOD AND DILUTION TUNNEL THEREFOR

This application is a continuation-in-part of application Ser. No. 08/111,843, filed Aug. 25, 1993 (still pending).

BACKGROUND OF THE INVENTION

1. Field of the Invention

This invention relates generally to the field of small engine control and specifically to an air/fuel mixture adjustment method using an improved dilution tunnel for collecting emission gasses.

2. Description of the Related Art

Exhaust emissions from internal combustion engines in automobiles and other vehicles are strictly regulated by the United States Government and other authorities. Emissions from vehicles and machines using smaller engines, such as chainsaws, lawn mowers, trimmers, and blowers are also a matter of concern. Most commonly these are two-stroke engines which are susceptible to scavenging losses and other phenomena which affect emissions and performance. Thus, numerous regulations and standards have been promulgated setting forth acceptable levels of emissions from such engines. Engines also must comply with regulations regarding air/fuel ratios. To measure emissions and determine compliance with the regulations, it is necessary to test the emissions and performance of such engines.

The air/fuel ratio of an engine is an important factor in measuring and controlling performance of the engine. If the mixture is too rich, the fuel does not burn completely, fuel is wasted, and unburned fuel (including HC and CO) is exhausted or fouls the engine. If the mixture is too lean, the engine loses power, knocks, or fails. The optimum mixture varies with the speed and operating conditions of the engine. Setting the air/fuel mixture of small engines is conventionally accomplished by adjusting one or more needle valves that control fuel flow in the carburetor.

As mentioned above, engine emissions are regulated by government and industry standards to reduce pollution and improve fuel economy. Therefore, it is advantageous to measure the air/fuel ratio to ensure compliance with the standards. More importantly, it is desirable to adjust or control the air/fuel ratio to achieve compliance with the standards or to achieve desired performance characteristics.

Numerous gas analyzers are known and available for determining the nature and quantities of the various components comprising the exhaust gas, including carbon monoxide, carbon dioxide, and hydrocarbons. Results are calculated based on measured levels in accordance with SAE J1088 and other standards.

To achieve accurate results it is necessary to properly collect the gas to be analyzed. In many cases, collection and testing are performed during final assembly of the machines or vehicles. Many engines are tested in succession by unskilled workers. Thus, gas collecting and testing apparatus should be simple to operate and easy to move from one engine to the next. One known collection method uses a probe inserted into a muffler of the exhaust system of an engine to be tested. The probe directs a sample of the exhaust to the analyzing apparatus. This method is relatively simple, but is highly dependent on the location of the probe. Different results are achieved at different locations and inaccurate results are obtained if the probe is not properly located. Typical causes of inaccuracies are incomplete mixing of the gasses in the muffler and introduction of atmospheric air into the sample. Inserting probes into the mufflers of engines on an assembly line is burdensome and prone to inconsistencies.

More consistent and accurate results have been achieved with an apparatus known as a mixing chamber, as described in SAE J1088. This is a heated metal box fastened to the outlet pipe of the muffler. The components of the exhaust gas are completely mixed in the chamber before being admitted to the sample probe and directed to the analyzing apparatus. The volume of the mixing chamber is at least 10 times, and usually 100 to 200 times, the cylinder displacement of the engine being tested. However, the size must be selected so that the temperature inside can be maintained at a level which will prevent hydrocarbons from condensing. The outlet of the chamber must be constructed so as not to have a tuning effect on the engine. The design of the chamber and the fastening means may affect engine performance, thus, mixing chambers are uniquely designed for each type of engine tested. Whereas mixing chambers are accurate, they are bulky, complex, and require substantial set-up time. Attaching the mixing chamber to engines on an assembly line is burdensome and time consuming. Maintaining adequate chamber temperature is an additional problem.

A dilution tunnel is another device used to collect the exhaust gasses for analysis. The dilution tunnel has one inlet which is fastened to the exhaust outlet pipe. A second inlet is connected to a source of dilution air or other gas which is to be mixed with the exhaust gas prior to analysis. It is well known in the art that it is desirable to dilute the exhaust gas with atmospheric air in a carefully controlled proportion. Dilution tunnels of this type are shown in U.S. Pat. Nos. 3,699,814; 3,817,100; 3,892,549; 3,965,749; 3,986,386; 4,586,367; 4,633,706; 4,654,058; 4,660,408; 4,747,297; 4,974,455; 5,058,440; 5,090,258; and 5,184,501. As with mixing chambers, the disadvantages of dilution tunnels according to the prior art are bulk, complexity, and long setup time. Also, it is necessary to fasten the tunnel to the exhaust outlet and a source of dilution air, which is troublesome in an assembly line where many engines are tested in succession.

Accordingly, it is desirable to have a device for collecting and analyzing exhaust gasses which is small, lightweight, and easily set up. Such a device should be adaptable for testing large numbers of engines in succession and should be simple and inexpensive to operate, while providing consistent and accurate results. The measured emissions of the engine should be used to determine and adjust the performance of the engine. In particular, the device should be connected to a system which allows measurement and adjustment of the air/fuel ratio in response to results of exhaust gas analysis for the engine.

SUMMARY OF THE INVENTION

The present invention provides a device for testing gaseous emissions from a source of those emissions. A dilution tunnel has an elongated, hollow tube. An inlet of the tube is adapted to be spaced from the source so as to admit emissions and surrounding air into the dilution tunnel through the inlet. Means are provided for analyzing the emissions in the tunnel.

The device is provided with a means for spacing the inlet from the source, such as a bracket, support, or handle. Since the tunnel is not fastened to the source, it can be supported by a robot or stationary support adjacent an assembly line carrying emissions generating engines. Thus, no operator is required to set up the tunnel. A probe located in the tunnel, such as a hollow tube opening toward the inlet, diverts emissions and air to analyzers outside the tunnel. Alternatively, sensors connected to the analyzing means are located in the tunnel. A means for facilitating mixing of the air and emissions, such as a screen, mesh or steel wool, is disposed in the tunnel downstream of the inlet.

A means for treating the emissions and air, such as a condenser, filter, water trap, or pump, is disposed between the probe and at least part of the analyzer.

A computer is connected to the analyzers to process data and control the analyzers. A fuel flow meter is connected to the computer and a fuel line, and a dynamometer is connected to the computer and a drive shaft. These are used to monitor engine performance with respect to emissions.

A method of testing gaseous emissions from a source is also disclosed. An inlet of a dilution tunnel comprising an elongated, hollow tube is located a selected distance from the source so as to be spaced from the source so as to admit emissions and surrounding air into the tunnel through the inlet.

The air and emissions in the tunnel are mixed. A portion of the emissions and air in the tunnel are diverted by a probe means disposed in the tunnel to a means for analyzing the emissions wherein the emissions diverted by the probe are the emissions analyzed.

Measured levels of CO and $CO_2$ are used to measure and adjust the air/fuel mixture of the engine. At air/fuel ratios richer than stoichiometric, that is where $\lambda$ (the relative air/fuel ratio) is less than 1, an equation can be derived to calculate air/fuel ratio of the engine based on a measured $CO/CO_2$ ratio. At air fuel ratios leaner than stoichiometric ($\lambda > 1$), the air/fuel ratio can be determined empirically using the measured values of CO and $CO_2$.

The present invention provides a method of adjusting an air/fuel mixture in an internal combustion engine. The steps include:
a) running the engine;
b) positioning a dilution tunnel near a source of engine emissions so as to admit emissions and surrounding air into the tunnel;
c) analyzing the emissions in the tunnel to determine an air/fuel ratio in the engine; and
d) adjusting the air/fuel mixture in response to the air/fuel ratio determined.

The step of running the engine includes running a two-stroke engine and/or running the engine at full speed. Additional steps include repeating steps c) and d) until a desired air/fuel ratio is achieved. Other steps may include:
e) running the engine at idle speed;
f) analyzing the emissions in the tunnel to determine the air/fuel ratio in the engine at idle speed mode; and
g) adjusting the idling air/fuel mixture in response to the air/fuel ratio determined.

Steps a), c), d), e), f), and g) may be repeated until a desired air/fuel ratio is achieved. The step of adjusting the idling air/fuel mixture includes adjusting a idle adjustment. The step of running the engine includes running the engine at idle speed or running the engine includes running the engine under a selected load.

Additional steps may include:
running the engine under at least a second load different from the selected load;
analyzing the emissions in the tunnel to determine the air/fuel ratio at the second load; and
adjusting the air/fuel mixture in response to the air/fuel ratio determined under the second load.

The step of positioning the dilution tunnel includes positioning an inlet of an elongated, hollow tube a selected distance from the source so as to be spaced from the source so as to admit emissions and surrounding air into the tunnel through the inlet. The step of adjusting the air/fuel mixture includes adjusting a valve on a carburetor that mixes air and fuel at an intake of the engine. Results of the emissions analysis can be recorded and reported by an output device.

The step of analyzing the emissions includes:
determining a relative air/fuel ratio ($\lambda$) according to the equation:

$$\lambda = \frac{\frac{x}{2} + y + \frac{u}{2} - \frac{b}{2}}{c}$$

where:
x and y are measured amounts of CO and $CO_2$ emissions, respectively;
a, b, and c are determined from a fuel being used where the fuel is $CH_aO_b$ and $$c = 1 + \frac{a}{4} - \frac{b}{2};$$

and
u is determined from the $CO/CO_2$ ratio and the fuel.

Also disclosed is a method of adjusting an air/fuel mixture in a two-stroke internal combustion engine having a carburetor for mixing air and fuel at an intake of the engine. The steps include:
a) running the engine;
b) positioning an inlet of a dilution tunnel comprising an elongated, hollow tube a selected distance from a source of engine emissions so as to be spaced from the source so as to admit emissions and surrounding air into the tunnel through the inlet;
c) analyzing the emissions in the tunnel to determine the air/fuel ratio in the engine by measuring $CO/CO_2$; and
d) adjusting the air/fuel mixture in response to the air/fuel ratio determined by adjusting a valve of the carburetor.

The invention also provides a method of analyzing emissions from an internal combustion engine, including the steps of:
a) running the engine
b) positioning an inlet of a dilution tunnel comprising an elongated, hollow tube a selected distance from a source of engine emissions so as to be spaced from the source so as to admit emissions and surrounding air into the tunnel through the inlet;
c) measuring CO and $CO_2$ emissions in the tunnel and determining a $CO/CO_2$ ratio; and
d) determining an air/fuel ratio of the engine from the $CO/CO_2$ ratio.

The step of determining the air/fuel ratio comprises:

determining a relative air/fuel ratio (λ) according to the equation:

$$\lambda = \frac{\frac{x}{2} + y + \frac{u}{2} - \frac{b}{2}}{c}$$

where:

x and y are measured amounts of CO and $CO_2$ emissions, respectively;

b and c are determined from a fuel being used where the fuel is $CH_aO_b$ and $$c = 1 + \frac{a}{4} - \frac{b}{2};$$

and u is determined from the $CO/CO_2$ ratio and the fuel.

Tests according to the invention have compared favorably with tests using a mixing chamber, while providing the advantages described herein. Using gas samples diluted by surrounding air results in less maintenance and cleaning of the analyzer and less frequent filter replacement. Dilution of the emissions with ambient air lowers the dew point of the emissions, which prevents condensation of hydrocarbons. Precise placement of the dilution tunnel and the degree of dilution are not critical for accurate measurements. One dilution tunnel can be used for many different types of engines without modification. Because there is no connection to the emissions source, there is no effect on engine performance.

The determination of the air/fuel ratio is simple and can be automated with a computer, for example. Air/fuel ratio data permit accurate and immediate adjustment of the air/fuel mixture.

BRIEF DESCRIPTION OF THE DRAWINGS

FIG. 3 shows a block diagram of an emissions analysis system according to one embodiment the invention;

FIG. 4 shows a detail view of the system according to another embodiment of the invention;

DESCRIPTION OF TEE PREFERRED EMBODIMENT

Figure 1:
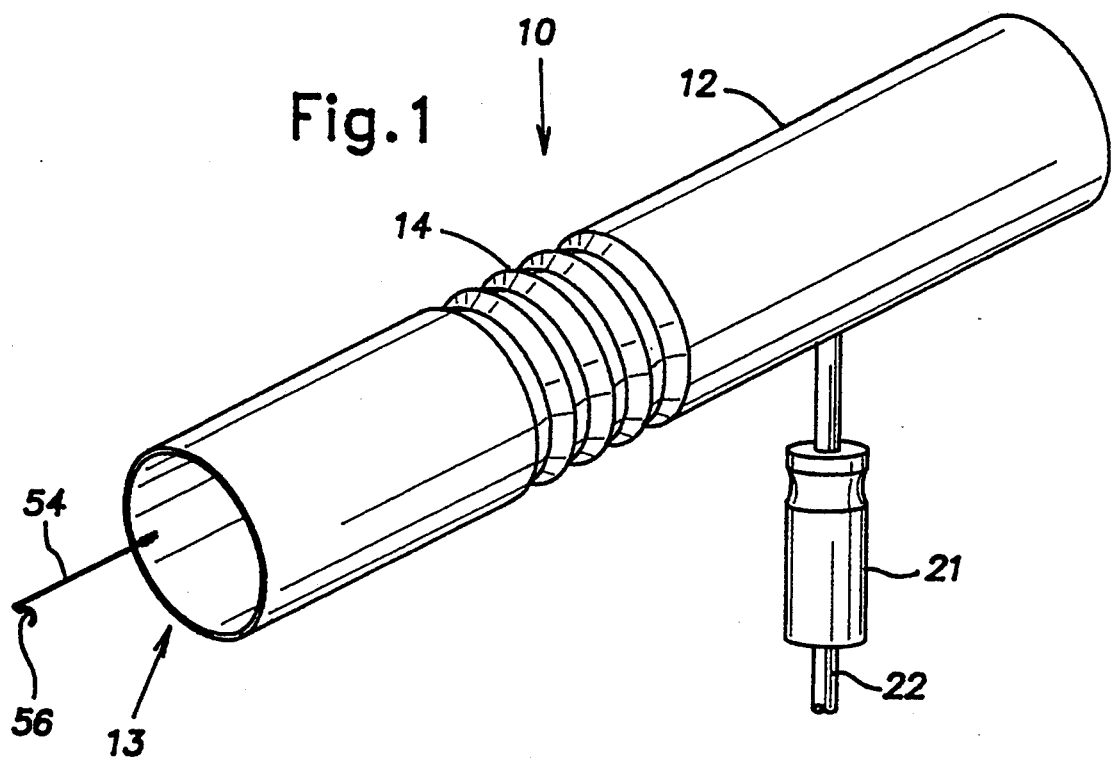
FIG. 1 shows an isometric view of a dilution tunnel according to the invention.

Referring to FIG. 1, a dilution tunnel 10 comprises an elongated, hollow tube 12 having an inlet 13 defined by an opening at an end of the tube 12. Preferably, the tube is a cylinder about 20 cm long, 5 cm in diameter, and made of aluminum, Polyvinylchloride, or other suitable rigid and relatively inert material. These materials are preferred for their availability, light weight, low cost, and because they will not interact with or pass emissions through their surfaces. The tube may have a flexible portion 14, such as a corrugated wall.

Figure 2:
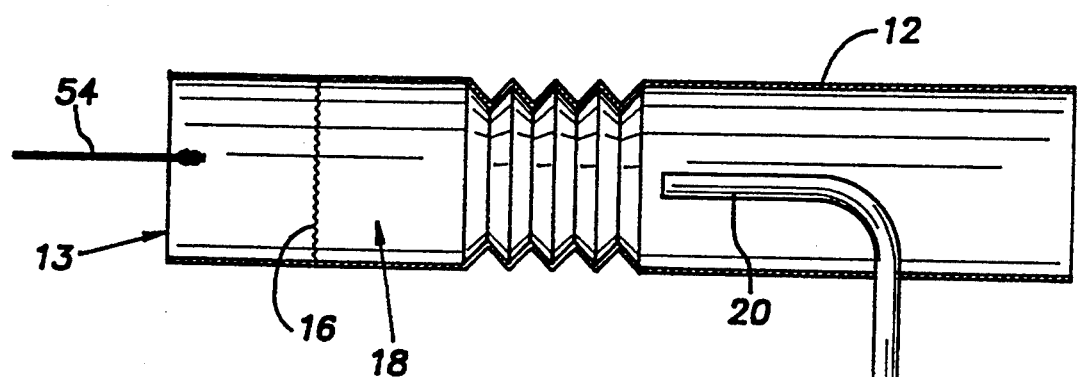
FIG. 2 shows a side view in section of the dilution tunnel of FIG. 1.

Referring to FIG. 2, a screen 16, wire mesh, steel wool, or other diffusing device is disposed inside the tube 12 and spans the interior circumference of the tube. The screen 16 and interior walls of the tube 12 define a mixing zone 18 on the opposite side of the screen from the inlet 13, that is, the downstream side of the inlet.

A probe 20, such as a hollow tube is disposed through a wall of the tube 12 downstream of the inlet 13. The probe is preferably curved 90° so as to pass through the wall orthogonally to the surface of the tube and open toward the inlet 13 of the tube. Part of the probe which extends outside the tube 12 is equipped with a handle 21.

Referring to FIG. 3, the probe 20 is connected to a sample line 22, such as a pipe or tube, adapted to convey gas to a gas analyzer 24. The gas analyzer 24 comprises apparatus for analyzing a plurality of components of a gas including a carbon monoxide analyzer 26, a carbon dioxide analyzer 28, an oxygen analyzer 30, an oxides of nitrogen analyzer 32, and a hydrocarbon analyzer 34. In one embodiment shown in FIG. 4, sensors 35 of the analyzers are disposed in the tunnel 10, thereby eliminating the need for the probe and sample line. Returning to FIG. 3, a means for treating the emissions and air, such as a condenser 36, is disposed between the sample line 22 and certain analyzers, as necessary. A filter 37 for removing heavy particulate matter is disposed upstream of the carbon monoxide and carbon dioxide analyzers. A water trap, a pump or other treating means may be disposed in the sample line 22 upstream of all or some of the analyzers as desired or required. A computer 38 is Preferably used to control the analyzer 24 and/or compile and record analysis data, which can be output to an output device, such as a printer 39a, a disk 39b, or a modem 39c. The recorded data can be reported to an agency or other party by means of the output device.

An engine 40 has an exhaust system including a muffler 42 and a tailpipe 44, the tailpipe being a source of emissions generated by the engine which is to be tested. These emissions are analyzed by the gas analyzer 24 to determine quantities of various components. The engine also includes a fuel line 46 for carrying fuel and a drive shaft 48 for transferring mechanical power.

For certain tests, such as air/fuel ratio analysis, it is preferable to use a fuel flow meter 50 connected to the fuel line 46 and the computer 38 to transmit fuel flow data to the computer. A dynamometer 52 is connected to the drive shaft 48 and the computer 38 to transmit engine speed and torque information to the computer. The fuel flow meter 50 and dynamometer 52 are not necessary to test emissions according to the invention, but are useful in measuring engine performance and other characteristics.

The dilution tunnel 10 is also provided with a means for spacing the inlet 13 from the tailpipe 44. The spacing means can be a spacer bracket 54, a scale, a support for the tunnel, or the handle 21 held by a person, for example. The spacer is used to maintain the inlet 13 of the tunnel at a relatively constant distance from the tailpipe 44. The bracket 54 has a notch 56 (FIG. 1) which is braced against an edge of the tailpipe to maintain constant spacing between the inlet and the tailpipe. Alternatively, the spacer bracket could rest on the muffler or another part of the engine. For example, one possible configuration comprises perforations 58 or other apertures in the tube upstream of the mixing screen 16, as shown in FIG. 4. It would be possible with such a configuration to use the end of the tube as the spacing means braced against the muffler 42 with the tailpipe 44 inside the tube so that dilution air enters through the perforations and the inlet 13 is effectively disposed upstream from the end of the tube near the screen 16. A wire extending across the inside of the tunnel near the inlet can be braced against the end of the tailpipe which is partly inside the tube 12. The inlet and the spacing means are such that no fixed connections to the sources of the emissions and dilution air are required and no separate or "artificial" means of urging or controlling flow of dilution air into the tunnel with the emissions is required. That is, the natural flow of emissions and air into the inlet provides sufficient dilution.

In operation, the engine 40 is running and emissions are directed from the engine, through the muffler and tailpipe, into the surrounding atmosphere. The dilution tunnel 10 is positioned so that its inlet 13 is spaced from the tailpipe 44 and emissions are directed through the inlet into the tube 12. The preferred distance is 1 to 2 cm, however, this is not critical. It is more important that the distance remain constant during analysis. Surrounding atmospheric air is entrained by the emissions flow and flows into the tube through the inlet 13 with the emissions. The air and emissions flow through the screen 16 where they are diffused and mixed in the mixing zone 18. Complete mixing of the gasses so that the components of the emissions are evenly distributed is important for accurate analysis of the emissions. A portion of the mixture flows into the probe 20 and is diverted, through the sample line 22, to the gas analyzer 24. The treatment means may condense, filter or otherwise treat the mixture prior to analyzing the various components of the emissions.

If, in addition to emissions data, information with respect to engine performance is desired, the dynamometer 52 and fuel flow meter 50 are connected as described above. The computer 38 compiles and analyzes data from the gas analyzer, dynamometer, and fuel flow meter to produce statistics regarding emissions content, engine performance, and relationships between these data.

Figure 5:
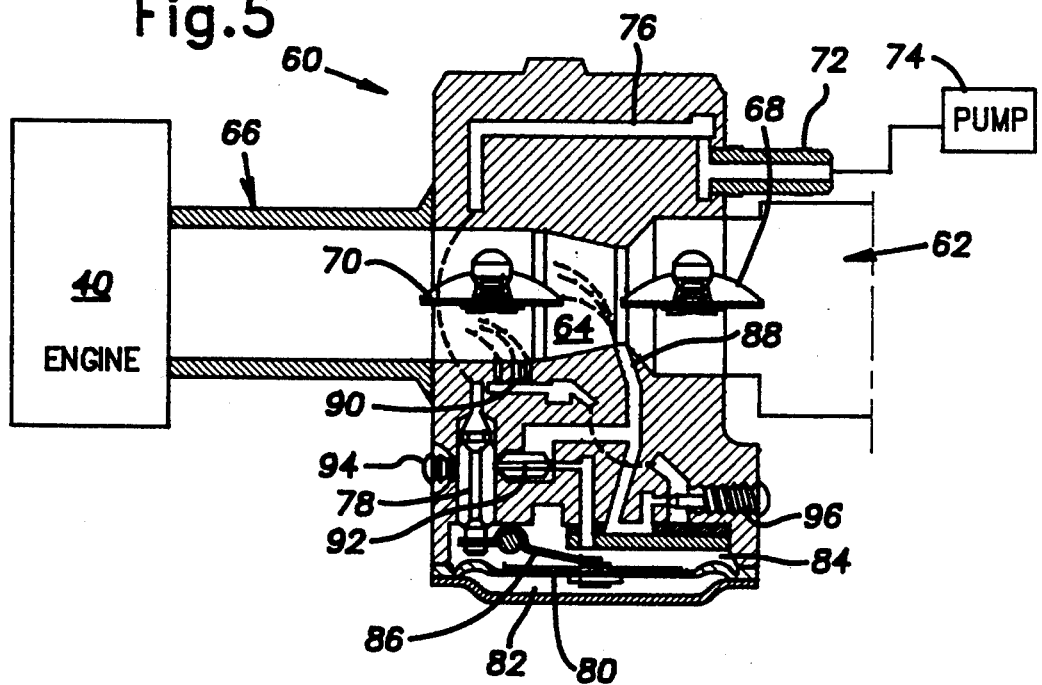
FIG. 5 shows a diaphragm carburetor commonly used in small engines.

FIG. 5 shows a membrane carburetor 60. The carburetor 60 includes an air intake 62 and a venturi 64 connected to an intake passage 66 or manifold of the engine 40. A choke 68 is provided in the air intake 62, and a throttle 70 is provided downstream of the venturi 64. A fuel intake 72 is connected to a fuel pump 74. A fuel conduit 76 connects the fuel intake 72 to an inlet valve 78.

A membrane 80 separates a metering chamber 82 from a fuel chamber 84. The membrane 80 is operatively connected to the inlet valve 78 by a linkage 86 so as to operate the inlet valve in response to negative pressure in the metering chamber 82. Thus, the flow of fuel into the fuel chamber 84 is regulated by the membrane 80.

The fuel chamber 84 is connected to a main fuel nozzle 88 and an idling fuel nozzle 90 by a arrangement of conduits. The main fuel nozzle 88 opens into the venturi 64, and the idling fuel nozzle 90 opens downstream of the venturi 64 near the throttle 70. A needle valve 92 adjustable by an air/fuel mixture adjustment screw 94 is disposed in the one of the conduits between the fuel chamber 84 and the fuel nozzles 88, 90. By advancing or retracting the air/fuel mixture adjustment screw 94, the amount of fuel being discharged through the carburetor can be adjusted, thereby adjusting the air/fuel mixture. An idle adjustment screw 96 is disposed in one of the conduits between the fuel chamber 84 and the idling fuel nozzle 90. The idle adjustment screw 96 is adjusted to control the flow of fuel to the idling fuel nozzle 90.

The carburetor 60 described is conventional and the adjustment screws are well known to those skilled in the art. Other means for adjusting the air/fuel mixture are known and need not be described in detail.

Returning to FIGS. 3 and 5, once data is collected by the gas analyzer 24, the data can be analyzed, as described below, to determine whether the air/fuel mixture of the engine is in compliance with applicable standards and whether the desired performance of the engine is being achieved. If not, the air/fuel mixture adjustment screw 94 and/or the idle adjustment screw 96 can be adjusted to achieve the desired air/fuel mixture.

Normally, the combustion reaction is described by the following or a similar equation:

$$CH_aO_b + c*\lambda*(O_2 + 3.773N_2) = \alpha CH_aO_b + x\, CO + y\, CO_2 + z\, H_2 + u\, H_2O + k\, NO_x + m\, O_2 + n\, N_2$$

This is adequate when testing four-stroke engines and diesel engines, but does not provide an adequate evaluation of two-stroke engine emissions because a major part of the hydrocarbon emissions result from scavenging losses. Therefore, modification is necessary. In addition, the equation must be adapted for use with analyses performed with the dilution tunnel 10 and gas analyzer 24 described herein. Thus, the modified equation, for stoichiometric or richer mixtures ($\lambda \leq 1$), is:

$$(CH_aO_b + c*\lambda*(O_2 + 3.773\, N_2) =$$
$$(1-\alpha)*(x\, CO + y\, CO_2 + z\, H_2 + u\, H_2O +$$
$$c*\lambda*3.773\, N_2)\,(\text{Combustion}) + \alpha*(CH_aO_b +$$
$$c*\lambda*(O_2 + 3.773\, N_2))\,(\text{Scavenging losses}) +$$
$$\gamma*(O_2 + 3.773\, N_2)\,(\text{Dilution})$$

where:
$\alpha$ = Scavenging loss factor; and
$\gamma$ = Dilution factor.
It is assumed that:

$$c = 1 + \frac{a}{4} - \frac{b}{2}$$

based on the fuel being used.

For the combustion portion of the equation, the assumption is made that all oxygen is burned, ($\lambda \leq 1$), and the $NO_x$ level $<<$ the $N_2$ level. For the HC emissions, the combustion portion of the equation is disregarded. Then, to calculate the dilution factor, it is necessary to calculate the air/fuel ratio and the scavenging loss factor. The air/fuel ratio is initially calculated for $\lambda < 1$. Because the types of exhaust analyzers are limited, CO and $CO_2$ are the only measured components that are used for calculating the air/fuel ratio, since they are combustion products. By using the $CO/CO_2$ ratio, the influence of the dilution is eliminated. Because only the combustion gases are used for the calculation, the equation can be simplified as follows:

$$CH_aO_b + c*\lambda*(O_2 + 3.773N_2) = x\, CO + y\, CO_2 + z\, H_2 + u\, H_2O + c*\lambda*3.773N_2$$

The hydrogen/water ratio is calculated according to the Spindt balance as:

$$\frac{H_2}{H_2O} = \frac{1}{3.5} \cdot \frac{CO}{CO_2}$$

The oxygen molar balance is:

$$\frac{b}{2} + c \cdot \lambda = \frac{x}{2} + y + \frac{u}{2}$$

and is rearranged as:

$$\lambda = \frac{\frac{x}{2} + y + \frac{u}{2} - \frac{b}{2}}{c}$$

The x/y ratio ($R_1$) is determined from the CO and $CO_2$ exhaust analyzers:

$$R_1 = \frac{x}{y} = \frac{[CO]}{[CO_2]}$$

The carbon balance is:

$$x + y = 1$$

Therefore:

$$x = \frac{1}{1 + \frac{1}{R_1}}; \quad y = \frac{x}{R_1}$$

The $H_2/H_2O$ ratio ($R_2$) is:

$$R_2 = \frac{z}{u} = \frac{R_1}{3.5}; \text{ and } z = \frac{uR_1}{3.5}$$

and the hydrogen balance is:

$$z + u = a/2$$

Thus:

$$z = \frac{\frac{a}{2}}{1 + \frac{1}{R_2}};$$

and $$u = \frac{z}{R_2} = \frac{a}{2(1 + R_1/3.5)}$$

Finally, the relative air/fuel ratio ($\lambda$) can be calculated using the equation:

$$\lambda = \frac{\frac{x}{2} + y + \frac{u}{2} - \frac{b}{2}}{c}$$

Where:
x and y are the measured amounts of CO and $CO_2$, respectively;
b and c are based on the fuel used; and
u is determined from the $CO/CO_2$ ratio and the combustion equation based on the fuel. That is:

$$u = \frac{a}{2(1 + R_1/3.5)}$$

Figure 6:
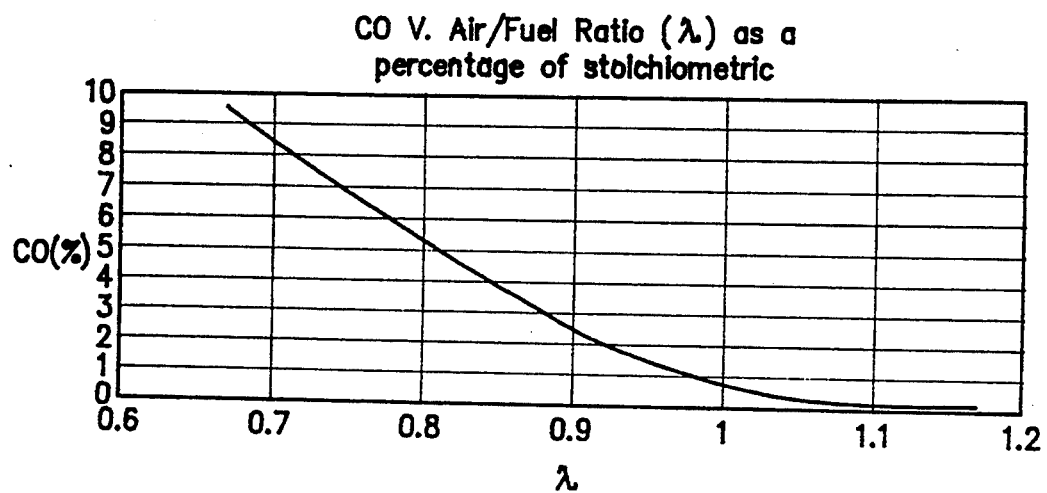
FIG. 6 shows a graph of Carbon Monoxide content of exhaust plotted against the relative air/fuel mixture (λ) as a percentage of stoichiometric for a two-stroke chainsaw engine using indolene fuel.

The equation for $\lambda$ is valid for $\lambda$ less than approximately 0.97. FIG. 6 shows CO emissions test data for a 2-stroke professional chain saw engine, Husqvarna 254, tested with a mixing chamber and Indolene fuel. The relative air/fuel ratio ($\lambda$) is calculated according to Spindt. Theoretically, the CO level should be zero at $\lambda = 1$ but due to incomplete mixing and combustion in the engine, there is a certain amount of CO even at mixtures leaner than stoichiometric.

Figure 7:
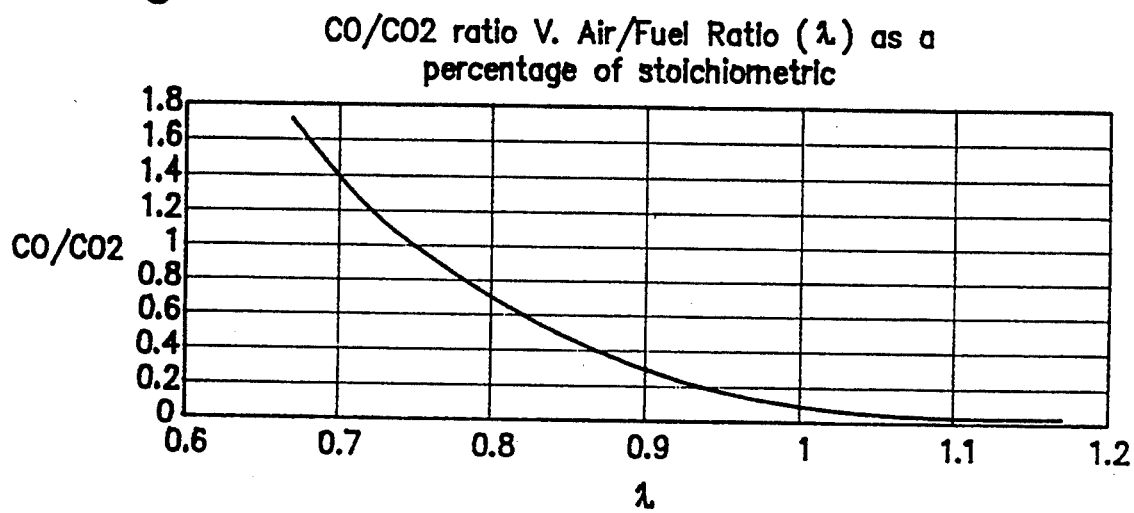
FIG. 7 is a graph of the Carbon Monoxide/Carbon Dioxide ratio plotted against the relative air/fuel ratio for the same engine and fuel used for FIG. 6.

It is not theoretically correct or possible to use the $CO/CO_2$ ratio to calculate the air/fuel ratio above stoichiometric mixture ($\lambda > 1$), but it is possible to use the actual measured ratios to determine the air/fuel ratio empirically. FIG. 7 shows the actual $CO/CO_2$ ratio for a 2-stroke engine tested with indolene fuel. This polynomial curve has been calculated by using test data from the Husqvarna 254:

$$\lambda = 1.1214 - 3.3098 R_1 + 24.42 R^2_1 - 62.939 R^3_1$$

where $R_1$ is equal to the measured $CO/CO_2$ ratio. This equation is useful for $0.95 < \lambda < 1.07$. To get highest possible accuracy, the tested engine should be mapped with the actual test fuel.

Because the preferred air/fuel ratio varies with engine speed, a preferred method of setting the ratio includes the steps of running the engine 40 at full speed, positioning the dilution tunnel 10 near the tailpipe 44, reading the air/fuel ratio and/or other data, adjusting the air/fuel ratio with the air/fuel mixture adjustment screw 94, running the engine at idle speed, and adjusting the idle adjustment screw 96. The various steps can be repeated as many times and at as many operating speeds and conditions as necessary to achieved the desired results. A simpler method includes running the engine, positioning the dilution tunnel 10 near the exhaust, reading the air/fuel ratio, and adjusting the air/fuel ratio with the air/fuel mixture adjustment screw 94.

The method described is adaptable to other types of carburetors, such as float-type, which have similar set screws for adjusting the air/fuel ratio. The method is also adaptable to other types of engines and air/fuel mixing apparatus, including fuel injectors, which are provided with means for adjusting the air/fuel ratio.

The present disclosure describes several embodiments of the invention, however, the invention is not limited to these embodiments. Other variations are contemplated to be within the spirit and scope of the invention and appended claims.

What is claimed is:

1. A method of adjusting an air/fuel mixture in an internal combustion engine, comprising the steps of:
   a) running the engine;
   b) positioning a dilution tunnel near a source of engine emissions so as to admit emissions and surrounding air into the tunnel;
   c) analyzing the emissions in the tunnel to measure a ratio of carbon monoxide and carbon dioxide to determine an air/fuel ratio in the engine; and
   d) adjusting the air/fuel mixture in response to the air/fuel ratio determined.

2. A method according to claim 1, further comprising the step of repeating steps c) and d) until a desired air/fuel ratio is achieved.

3. A method according to claim 1, wherein the step of running the engine includes running a two-stroke engine.

4. A method according to claim 1, wherein the step of running the engine includes running the engine at full speed.

5. A method according to claim 4, further comprising the steps of:
   e) running the engine at idle speed;
   f) analyzing the emissions in the tunnel to determine the air/fuel ratio in the engine at idle speed; and
   g) adjusting the idling air/fuel mixture in response to the air/fuel ratio determined.

6. A method according to claim 5, further comprising the step of repeating steps a), c), d), e), f), and g) until a desired air/fuel ratio is achieved.

7. A method according to claim 5, wherein the step of adjusting the idling air/fuel mixture includes adjusting an idle adjustment.

8. A method according to claim 1, wherein the step of running the engine includes running the engine at idle speed.

9. A method according to claim 1, wherein the step of running the engine includes running the engine under a selected load.

10. A method according to claim 9, further comprising the steps of:
    running the engine under at least a second load different from the selected load;
    analyzing the emissions in the tunnel to determine the air/fuel ratio at the second load; and
    adjusting the air/fuel mixture in response to the air/fuel ratio determined under the second load.

11. A method according to claim 1, wherein the step of positioning the dilution tunnel includes positioning an inlet of an elongated, hollow tube a selected distance from the source so as to be spaced from the source so as to admit emissions and surrounding air into the tunnel through the inlet.

12. A method according to claim 1, wherein the step of adjusting the air/fuel mixture includes adjusting a valve on a carburetor that mixes air and fuel at an intake of the engine.

13. A method according to claim 1, further comprising the step of recording results of the emissions analysis and reporting the results by an output device.

14. A method according to claim 1, wherein the step of analyzing the emissions includes:
    determining a relative air/fuel ratio ($\lambda$) according to the equation:

$$\lambda = \frac{\frac{x}{2} + y + \frac{u}{2} - \frac{b}{2}}{c}$$

where:
   x and y are measured amounts of CO and $CO_2$ emissions, respectively;
   a, b, and c are determined from a fuel being used where the fuel includes $CH_aO_b$ and $$c = 1 + \frac{a}{4} - \frac{b}{2};$$

and
   u is determined from a $CO/CO_2$ ratio and the fuel.

15. A method of adjusting an air/fuel mixture in a two-stroke internal combustion engine having a carburetor for mixing air and fuel at an intake of the engine, comprising the steps of:
   a) running the engine;
   b) positioning an inlet of a dilution tunnel comprising an elongated, hollow tube a selected distance from a source of engine emissions so as to be spaced from the source so as to admit emissions and surrounding air into the tunnel through the inlet;
   c) analyzing the emissions in the tunnel to determine an air/fuel ratio in the engine by measuring a CO/CO ratio; and
   d) adjusting the air/fuel mixture in response to the determined air/fuel ratio by adjusting at least one valve of the carburetor.

16. A method of analyzing emissions from an internal combustion engine, comprising the steps of:
   a) running the engine;
   b) positioning an inlet of a dilution tunnel comprising an elongated, hollow tube a selected distance from a source of engine emissions so as to be spaced from the source so as to admit emissions and surrounding air into the tunnel through the inlet;
   c) measuring CO and $CO_2$ emissions in the tunnel and determining a $CO/CO_2$ ratio; and
   d) determining an air/fuel ratio of the engine from the $CO/CO_2$ ratio.

17. A method according to claim 16 wherein the step of determining the air/fuel ratio comprises:
   determining a relative air/fuel ratio ($\lambda$) according to the equation:

$$\lambda = \frac{\frac{x}{2} + y + \frac{u}{2} - \frac{b}{2}}{c}$$

where:
   x and y are measured amounts of CO and $CO_2$ emissions, respectively;
   a, b, and c are determined from a fuel being used where the fuel includes $CH_aO_b$ and $$c = 1 + \frac{a}{4} - \frac{b}{2};$$

and
   u is determined from a $CO/CO_2$ ratio and the fuel.

18. A method according to claim 16, further comprising the step of empirically determining a polynomial representing the air/fuel ratio as a function of the $CO/CO_2$ ratio.

* * * * *

UNITED STATES PATENT AND TRADEMARK OFFICE
CERTIFICATE OF CORRECTION

PATENT NO. : 5,450,749
DATED : September 19, 1995
INVENTOR(S) : Strom et al.

It is certified that error appears in the above-indentified patent and that said Letters Patent is hereby corrected as shown below:

Column 5, line 56, delete "TEE" and insert --THE--.

Column 10, line 24, delete "$\lambda=1.1214-3.3098R_i+24.42R_i^2-62.939R_i^3$," and insert --$\lambda=1.1214-3.3098R_i+24.42R_i^2-62.939R_i^3$--.

Column 12, line 23, (Claim 15, line 13), delete "CO/CO" and insert --$CO/CO_2$--.

Signed and Sealed this

Nineteenth Day of December, 1995

*Attest:*

BRUCE LEHMAN

*Attesting Officer*  *Commissioner of Patents and Trademarks*